(12) United States Patent
Moore (10) Patent No.: US 6,533,736 B1
(45) Date of Patent: Mar. 18, 2003

(54) WIRELESS MEDICAL STETHOSCOPE

(76) Inventor: Mark Moore, 623 Chancey La., Tallahassee, FL (US) 32308

(*) Notice: Subject to any disclaimer, the term of this patent is extended or adjusted under 35 U.S.C. 154(b) by 148 days.

(21) Appl. No.: 09/579,486

(22) Filed: May 30, 2000

(51) Int. Cl.⁷ .................................................. A61B 7/04
(52) U.S. Cl. ....................... 600/586; 181/131; 600/528; 381/67
(58) Field of Search ................................ 600/586, 528; 181/131, 132; 381/67; D3/203

(56) References Cited

U.S. PATENT DOCUMENTS

| | | | |
|---|---|---|---|
| 3,160,708 A | 12/1964 | Andries et al. | |
| 3,851,123 A * | 11/1974 | Lipinski et al. | 181/135 |
| 4,248,241 A * | 2/1981 | Tacchi | 128/903 |
| 4,335,281 A * | 6/1982 | Scott et al. | 379/430 |
| 4,723,555 A | 2/1988 | Shue | 128/715 |
| 4,777,961 A | 10/1988 | Saltzman | 128/715 |
| 4,878,501 A * | 11/1989 | Shue | 600/493 |
| 5,027,825 A * | 7/1991 | Phelps et al. | 600/528 |
| 5,159,639 A * | 10/1992 | Shannon et al. | 381/312 |
| 5,327,178 A * | 7/1994 | McManigal | 351/158 |
| 5,406,953 A * | 4/1995 | Bui | 600/490 |
| 5,557,681 A * | 9/1996 | Thomasson | 327/553 |
| 6,010,216 A * | 1/2000 | Jesiek | 351/158 |
| 6,340,350 B1 * | 1/2002 | Simms | 600/528 |

* cited by examiner

Primary Examiner—Kennedy Schaetzle
(74) Attorney, Agent, or Firm—Carnes & Cona (57) ABSTRACT

A wireless stethoscopic apparatus is disclosed comprising of an auscultation piece removably secured to a hearing piece. The components, auscultation piece and hearing piece, when not in use can be stored in a carrying case. Housed within the auscultation piece is a conventional radio frequency chip including a microphone that will enable transmission of radio frequency without the use of wires. A transmission system is housed within the auscultation piece, while the hearing piece includes a link manager receiver device for receiving the radio signals wirelessly from the transmission system and enabling sound to be heard via the hearing device from the auscultation piece.

17 Claims, 5 Drawing Sheets

WIRELESS MEDICAL STETHOSCOPE

BACKGROUND OF THE INVENTION

1. Field of the Invention

The present invention relates generally to a novel and unique multifunctional wireless medical stethoscope to be used by health care professionals or the like for diagnosing patients and more particularly to a unique and novel multifunctional wireless medical stethoscope that includes a small microchip that operates in a globally available frequency band ensuring communication compatibility worldwide to auscultate human/animal organs and structural sounds for wireless transmission from the patient to an earpiece worn by the user.

2. Description of the Prior Art

The most common stethoscope primarily in use today by almost all health care professionals is the manual stethoscope. The manual stethoscope has had no significant design changes since the late 1800's. The manual stethoscope consists of a listening piece with a diaphragm with sound being transmitted to the practitioners ears via a "Y-tubing". However, due to this connecting tube, the practitioner is very limited in his proximity to the patient, innately causing the physical sounds transmitted to be less than ideal.

In addition to the manual stethoscope, electronic stethoscopes have been developed which use electronic wires to transmit sound detected at the listening diaphragm to another device that reconverts the transmission to sound. This technology has not substantially changed for over 40 years.

It is evidenced in the prior art that numerous attempts have been made to address the problems associated with the manual and electronic stethoscopes. For example, U.S. Pat. No. 4,723,555 issued to Shue discloses a type of radio/wire stethoscopic apparatus designed for multiple auscultatation and historical recording of a patient. The circular diaphragm and Y-piece provide an overall structure of the device, which is similar to the manual stethoscope in use today. In addition, sound is received via the circular diaphragm is converted to electrical signals and transmitted through a radio/recorder set and an interface of audio wave control device that is electrically coupled to the unit for enabling the wearer to hear the received sound. Thus, providing for a stethoscope that still provides a restricted amount of distance between him and the patient, inherently providing a unit, unlike the present invention, that does not reflect the most advanced technology available today.

Yet another example is seen in U.S. Pat. No. 4,248,241 issued to Tacchi wherein disclosed is patient monitoring apparatus which employs transmitter and receiver units. The practitioner is still physically connected to the patient with this device unlike the present invention which is totally wireless.

U.S. Pat. No. 4,777,961 issued to Saltzman relates to a soley patient mounted and supported constant monitoring suction stethoscopic and radio transmitter system and remote radio receiver and speaker. This device features a box-like structure which is clipped on to the practitioners shirt thereby acting as a loud speaker, broadcasting the precordial sounds out publicly.

In addition, U.S. Pat. No. 3,160,708 issued to Andries et al relates to an electronic stethoscope adapted for diagnostic uses and effective to reproduce heart sounds substantially approximating the conventional acoustical stethoscope. This device has no wireless components and unlike the present invention features dated technology.

As observed, none of the previous inventions as described above have been utilized by the medical community. Thus, it is seen that these previous efforts do not provide the benefits intended with the present invention or method, such as providing a wireless stereoscopic apparatus that ultimately delivers exceptional quality and telecommunication capability. The present invention provides a medical/educational stereoscopic device which features practicality and uniqueness, by enabling wireless communication between the patient and health care professional when diagnosing occurs, and consequently provides an apparatus that would be quickly adopted and used successfully by the medical community. Additionally, prior techniques do not suggest the present inventive combination of component elements as disclosed and claimed herein.

Accordingly, it is seen that there is a need for a wireless medical stethoscope designed and configured to offer the most advanced technology available today to the medical community. This medical device is compact, easy to use, and has the advantage of allowing freedom of movement and distance between the practitioners and their patient. There is no connecting tube to limit the practitioners proximity to the patient or to reduce the sound perception. Additionally, the wireless medical stethoscope can be used by health care professionals of all types.

Thus, as will be seen, the present invention achieves its intended purposes, objectives and advantages over the prior art device by accomplishing the needs and objectives as identified herein, through a new, useful and unobvious combination of component elements, which is simple to use, with the utilization of a minimum number of functioning parts, at a reasonable cost to manufacture, assemble, test and by employing only readily available materials.

SUMMARY OF THE INVENTION

The present invention is a novel and unique wireless medical stethoscope that will advance the state of the art of medicine by providing a higher level of patient care. This novel and unique wireless stethoscope device is designed to be compact in size and requiring a minimal amount of components so as to adequately and successfully operate and manipulate the present invention.

To enable a wireless stethoscope, the present invention comprises an auscultation piece, an earpiece, and a holding case for allowing easy storage and transporting capabilities of the auscultating piece and earpiece when not in use. Each component, including the ausultation piece, earpiece, and carrying case are separate structural entities.

Constructionally, the auscultation piece comprises a pyramidal shape have an upper end and a lower end. The upper end is smaller in size than the lower end, thus providing for the pyramidal shape. Located on the side wall of the auscultation piece is a plurality of indentations or grooves. These grooves form the typical finger positioning of the examining physician or practitioner and thus provide for an apparatus that is easy and efficient to use.

Located on the lower end of the auscultation piece is a sound receptor panel or diaphragm for enabling auscultation of the patient. Embedded within the auscultation piece is a conventional radio frequency chip designed and configured for wireless transmission. Preferably, this microchip will operate in a globally available frequency band with a link manager ensuring communication compatibility worldwide, thus increasing the usability and functionality of the stethoscope apparatus of the present invention.

Activation can occur manually by depressing a button located exteriorly on the auscultation piece, or optionally can be voice activated. When not in use the auscultation piece can be coupled to the earpiece for storage. This will provide for the earpiece to be removably secured to the auscultation piece consequently providing for a compact unit, when not in use.

The earpiece structurally includes a frame having a first end, a second end and a middle section sandwiched therebetween. The first end, second end and middle section form a substantially J-shape configuration. It is noted that this frame is fabricated from a durable, yet flexible material, so as to allow for the wearer to adjust the overall structure of the frame so as to enable it to conform to their particular shape. Pivotally secured to the second end is a hearing piece. This hearing piece is conventional in design and thus, is configured to be inserted into the ear of the user for allowing adequate and comfortable listening compabilities. Embedded within the main frame is a link manager receiver device. The link manager receiver is in communication with the auscultation piece, so as to receive the sounds when the auscultation piece is placed on the patient. Located on the mainframe and coupled to the link manager receiver device is a sound adjustment unit. This sound adjustment unit is a conventional mechanical device that is utilized for adjusting the volume for the sounds received via the link manager receiver.

For providing removable attachment capabilities, the auscultation piece and earpiece can include corresponding locking means. This will provide for the auscultation piece and earpiece to be removably secured to each other and thus provides a device, when not in use, to be stored as a singular entity. The locking means is conventional and can be any locking means that will ensure quick and efficient release and engagement of the earpiece to the auscultation piece. The auscultation piece and the earpiece mate together to then fit into a holder device. This holder device can further include conventional attachment mechanism, such as the use of clips for rendering attachment to the pants or jacket of the health care professional.

This novel and unique wireless stethoscope device provides faster throughput and better reliablity than present systems. Since the sound is transmitted wirelessly, quality is not lost wherein with conventional stethoscopes the sound waves must travel through the Y-piece tubing to the listening ear. Any amount of traveling will reduce the quality of sound being heard by the health care professional.

Normally in the use of the manual stethoscope or the electronic stethoscope the following problems may be encountered: i. The mobility of the physician or practitioner is generally quite limited. ii. The quality of the sound for diagnosis may be compromised. iii. The state of the art of the technology is often lacking. Thus, the present manual and electronic stethocopes often do not offer the physician or practitioner the opportunity to achieve a higher level of patient care and greater productivity by being able to rapidly monitor and detect the onset of medical problems while being totally free of any physical connection to the patient.

Using and operating the present invention is simple, easy, and extremely efficient. The present invention will elevate the role of the stethoscope in modern medicine. In addition, the novel and unique wireless medical stethoscope will advance the technology in the art of stethoscopes.

Accordingly, it is an object of the present invention to provide for a wireless medical stethoscope device that will overcome the deficiencies, shortcomings, and drawbacks of prior medical stethoscope devices.

Another object of the instant invention is to provide a wireless medical stethoscope which will not limit the mobility of the practitioner or limit the use of his hands to the length of the stethoscope tubing, but provides the ability to privately hear all the medical sounds as in the original manual stethoscope.

Still another object of the present invention is to provide a novel method of use of the wireless medical stethoscope such that the novel device is completely portable and can be rapidly activated.

A further object of the present invention is to provide a wireless medical stethoscope device which is light weight and simple in design so as to provide for a medical device which can provide for a more efficient and effective process for assessing, monitoring and detecting the onset of medical problems. This medical device will provide for an option for programmable versions for teaching purposes, telemedicine conferencing as well as a loudspeaker means.

Yet another object of the present invention is to provide for a novel and unique medical device which can provide improved continuous assessing and monitoring of the patient, including, but not limed to those undergoing surgical procedures, obstetrics delivery, emergency medical trauma, or the like.

Another object of the present invention is to provide for a novel and unique wireless medical stethoscope which can be used on both human and animal patients.

Still a further object of the present invention, to be specifically enumerated herein, is to provide a medical device in accordance with the preceding objects and which will conform to conventional forms of manufacture, be of simple design and easy to use so as to provide a medical device that will be economically feasible, long lasting and relatively trouble free in operation.

Although there have been many inventions related to stethoscope medical devices, none of the prior art related to the present invention has been designed to provide the most advanced technology available today. The present invention meets the requirements of simplified design, compact size, low initial cost, low operating cost and ease of maintainability.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, a fuller understanding of the invention may be had by referring to the detailed description of the preferred embodiments in addition to the scope of the invention defined by the claims taken in conjunction with the accompanying drawings.

FIG. 16 is a block diagram, illustrating the electrical components utilized with the medical device of the present invention.

Similar reference numerals refer to similar parts throughout the several views of the drawings.

DESCRIPTION OF THE PREFERRED EMBODIMENT

As seen in the drawings, in particular to FIGS. 1–15 thereof, the first embodiment of the present invention, a novel and unique medical device for wireless medical stethoscopes, denoted by reference numeral 10 (see assembled stored apparatus illustrated in FIG. 1 and disassembled in FIG. 2) will be described herein. Shown is a wireless medical stethoscope device 10 (see FIG. 1 and FIG. 2), which comprises an earpiece apparatus 12 (see FIGS. 1–9), an auscultation piece apparatus 14 (see FIGS. 1, 2 and 10–14), and a holding device 16 (see FIGS. 1, 2 and 15). It is noted that the embodiment illustrated in FIGS. 1–9 illustrates an earpiece apparatus that is to be used on a right ear. The embodiment for the left ear is not illustrated, but it is to be understood that this left ear embodiment will be substantially the same shape, size and configuration, with the exception of being a mirror image, of the embodiments shown in the figures. Thus, this left ear configuration will not be separately illustrated.

As seen in FIGS. 1–15, the ear piece apparatus 12 is removably lockable to the auscultation piece apparatus 14 to provide for a singular unit when not in use on a patient and when in the locked storable position. This will provide for the ear piece and auscultation piece to form a lockable unit that is removably secured to the holding device 16. The holding device 16 will maintain the ear piece and auscultation piece in a storable and protected environment.

The object of the present invention is to provide for a medical stethoscope that is not only wireless, but one that is compact in size and which will produce a higher quality of sound than conventional stethoscope, also known as a manual stethoscope. In order to achieve this wireless system, the present invention includes the removable components including the ear piece apparatus 12 and auscultation piece apparatus 14.

In use, the health care professional will remove the unit (earpiece locked to the auscultation piece) from the holding device. In the preferred embodiment, the unit is removed from the holder and, in one swift motion, the practitioner's will secure the earpiece to his ear, wherein the listening portion of the earpiece is placed firmly to the ear. Once secured thereto, the auscultation piece is removed (disengaged from the earpiece) therefrom (see FIG. 2). The auscultation piece is placed on the patient's body in the area to be auscultated. The present invention can then be utilized efficiently and accurately.

As seen in FIGS. 1 through 9, the earpiece comprises a mainframe 18 having a first end or post auricular 20, a second end or pre-auricular 22 and a middle portion (illustrated, but not labeled) therebetween. This frame forms a substantial J-shape configuration for rendering a frame that will accept and rest comfortably on the ear. This middle portion of the frame, in the preferred embodiment, is fabricated from a durable, yet resilient and pliable material, such as polymer, polymer-coated metal, or the like. This will enable the earpiece to be adjustable by allowing the user to bend and adjust the pliable frame to conform to the size and shape of the wearer's ear. Thus provide for a more comfortable and accurate fit.

As seen in FIGS. 3–9, the first end 20 includes an opening or aperture (illustrated, but not labeled). This opening or aperture is optional, and is provided if the user wishes to doubly secure the earpiece. In one embodiment, a small rope, string or the like, is secured to this aperture, and its opposites ends are joined securely for innately forming a closed loop configuration. In this design, when the earpiece is secured to the ear, the user can wrap the closed loop around their ear and around one of the posts. This will doubly secure the earpiece to the user. The circumference of the loop should be of an adequate size so as to enable a comfortable and secured fit thereon. Thus, this circumference should be approximately, but not limited to, 2.5 to 4.5 inches. Alternatively, the material used for the rope, string or the like can possess resilient properties. This arrangement of doubly securing the earpiece to the wearer is ideally suited for those who work in a busy environment such as a trauma physician running a code blue or the like.

In an alternative configuration, the aperture can accept a longer rope, string, chain or the like, wherein, its opposite ends are secured in order to form a larger closed loop. This arrangement will allow the earpiece to hang from a string, chain, clip or the like. The closed loop can be located around the user's neck, clipped to their nametag or the like.

Figure 7:
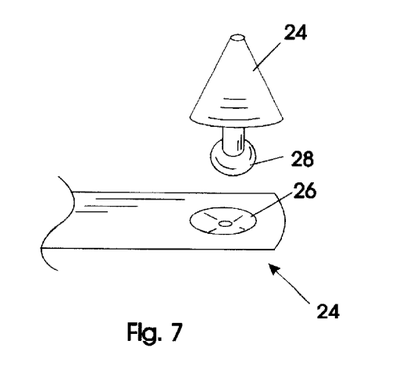
FIG. 7 is an enlarged perspective view of the adjusting mechanism used with the hearing portion of the earpiece used in the medical device of the present invention.

Located at the opposite end or second end 22 is the hearing portion 24. This hearing portion 24 is substantially conventional and will be placed within the ear of the wearer or user and thus includes a speaker located therein. To add to the comfort of the earpiece, this portion can be altered via an adjusting device. As shown in FIG. 7, the adjusting device preferably is a ball and socket configuration. This will provide for the frame to include a groove 26, which will act as a socket. The hearing portion 24 will include a ball segment 28, thus rendering for the ball segment to rest within the socket 26 of the frame and allow it to rotate freely therein. This will provide for a hearing portion that is adjustable, and one that will adjust naturally to the user. Optionally, a screw or the like can be used for locking and securing the ball segment within the socket.

Figure 8:
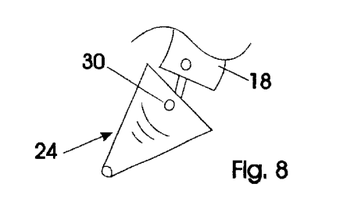
FIG. 8 is an enlarged side view of an alternative embodiment for the adjusting mechanism used with the hearing portion of the earpiece used in the medical device of the present invention, in the disengageable position.
Figure 9:
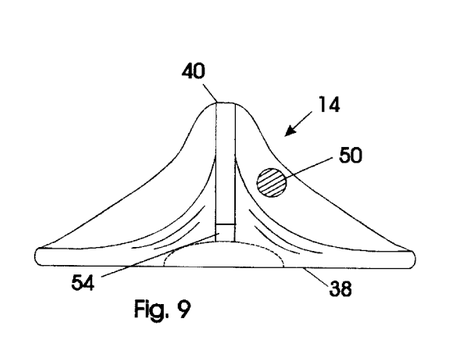
FIG. 9 is a first side view of the auscultation piece used in the medical device of the present invention, in the disengageable and useable position.
Figure 10:
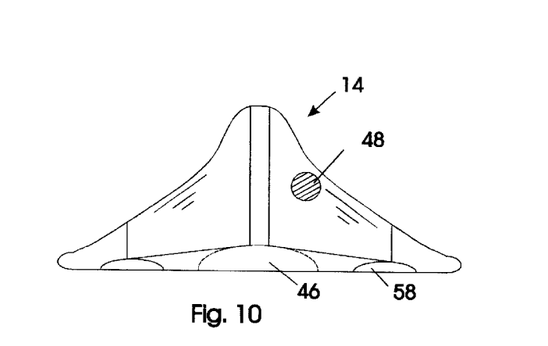
FIG. 10 is a second side view of the auscultation piece used in the medical device of the present invention, in the disengageable and useable position.

The adjusting device can be altered to provide for the hearing piece 24 to be pivotally secured to the second end 22 of the main frame 18. This alternative configuration is shown in FIG. 8. As seen, the pivotal attachment is conventional, and thus provides for the hearing piece 24 to pivot freely about pivot rod 30. This rod can have a threaded end, so that this hearing piece 24 can be locked by allowing a nut or the like to rotate about the threaded end and lock the hearing piece 24 in a fixed and secured position.

Alternatively, this hearing piece 24 can be secured to the second end 22 of the main frame 18 by way of a hollow flexible shaft. In this configuration, the shaft can be bent to the desired angular placement for providing a comfortable and accurate fit. In this configuration, the locking mechanism for locking the hearing piece in a fixed position is eliminated.

Extending upwardly from the curved area or center area of the frame of the earpiece 12 is the securing unit 32. This securing unit 32 is used to secure the earpiece 12 to the auscultation piece 14 when the device is not in use. This securing unit 32 will be discussed in further detail when discussing the receiving unit of the auscultation piece 14 for receiving the securing unit.

Figure 5:
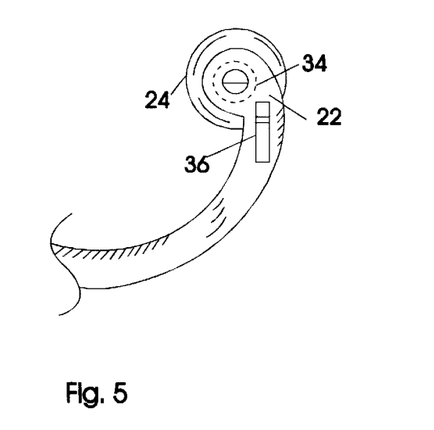
FIG. 5 is an enlarged bottom view of the earpiece used in the medical device of the present invention, in the disengageable and useable position.
Figure 6:
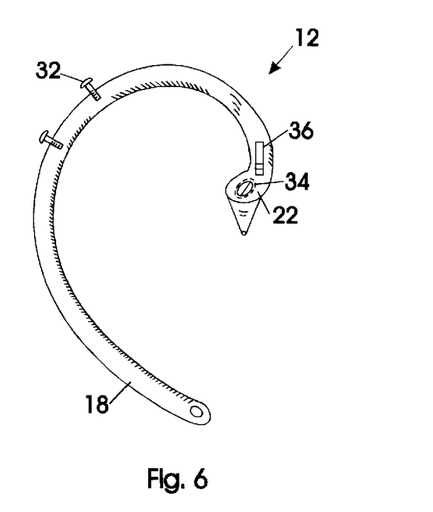
FIG. 6 is a perspective view of the earpiece used in the medical device of the present invention, in the disengageable and useable position.

Externally located within the frame 18 of the earpiece 12 is a link manager receiver device 34 (illustrated in outline in FIGS. 5 and 6). This link manager receiver device 34 works in combination with the auscultation piece for enabling the sound auscultated from the portion of the body to be received and heard by the earpiece 12.

Figure 4:
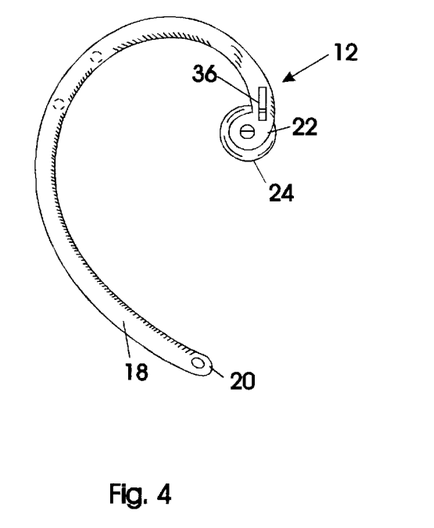
FIG. 4 is a bottom plan view of the earpiece used in the medical device of the present invention, in the disengageable and useable position.

The sound that is transmitted can be controlled via a conventional volume control knob 36 as seen in FIGS. 4–6. In this arrangement, the user can amplify or de-amplify the sounds so as to suit their particular needs. This feature not only enhances the final product, but enables those with impaired hearing and those with presbyascusis to still practice in the medical profession, due to the ability of increasing the volume of the wireless stethoscope of the present invention and allowing them to adequately hear the desired sounds.

The auscultation piece 14, illustrated in FIGS. 1, 2, and 9 through 13 is designed and configured to be handled easily, efficiently and accurately. In order to do so, the auscultation piece 14 includes a unique design and configuration. As seen, the auscultation piece includes a lower portion or inferior 38 and an upper portion or superior 40. The lower portion is larger is size than the upper portion so as to provide for an overall pyramidal shape. As further seen, located along the side wall of the auscultation piece 14 are four indentations or recesses 42. These indentations are designed and configured to receive the tips of the first digit (thumb), second digit (index finger), third digit (middle finger), and the tip of the fourth digit (ring finger). The user may wish not to use this fourth indentation. The recesses provide efficient gripping capabilities for enabling adequate manipulation of the auscultation piece. Optionally, the lower portion can further include a flange (see FIG. 10), illustrated but not labeled, that will be used in combination with the carrying case. This will allow for the auscultation piece to slide within the carrying case via the use of the flange.

Embedded within the auscultation piece is a conventional radio frequency chip 44 (illustrated in outline). This chip is conventional and is structured so as to operate in a globally available frequency band ensuring communication compatibility worldwide to auscultatate humans/animals, organs, structural sounds, or the like, for wireless transmission. This microchip will allow for the user to operate the unit wireless, and thus enable the transmitter to transmit the signals successfully and innately allow for adequate transmission from the auscultation piece to the earpiece. The most recent advanced chip technologically available, which has been used to achieve favorable results, is the chip known as the Bluetooth chip. This chip is ideal for use in wireless communication networks, although simplified chips utilizing any radio frequency range can also be used in the medical device of the present invention.

Figure 12:
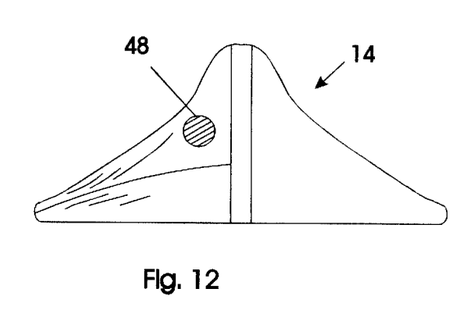
FIG. 12 is a third side view of the auscultation piece used in the medical device of the present invention, in the disengageable and useable position.

Located in the auscultation piece, as seen FIG. 12, is a diaphragm 46. This diaphragm is designed and configured to procure the sounds for transmission from the auscultation piece to the earpiece. This diaphragm, also known as the auscultation panel includes a condenser microphone and is of a conventional design.

Figure 1:
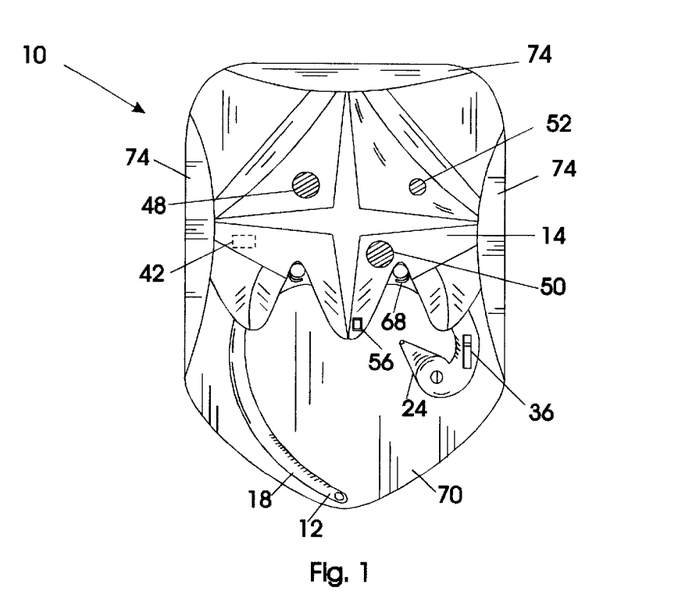
FIG. 1 is a top plan view of the medical device of the present invention in an assembled and storable position.
Figure 2:
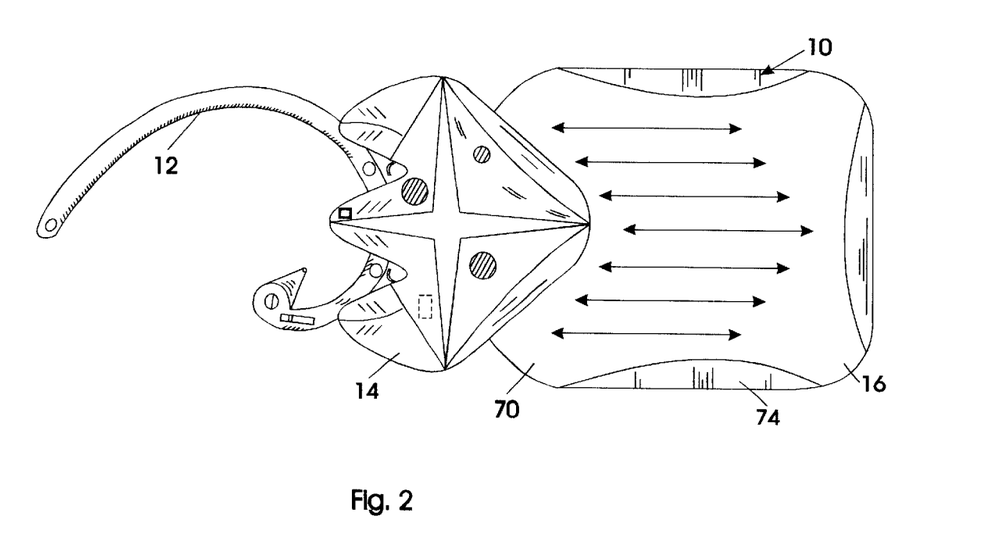
FIG. 2 is a top plan view of the medical device of the present invention, with the earpiece disengaged from the auscultation piece and both pieces [being] removed from the holding case.
Figure 3:
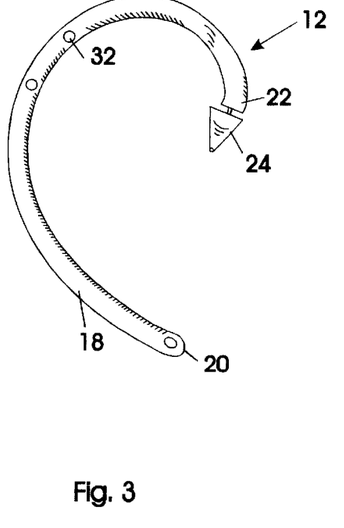
FIG. 3 is a side plan view of the earpiece used in the medical device of the present invention, in the disengageable and useable position.
Figure 13:
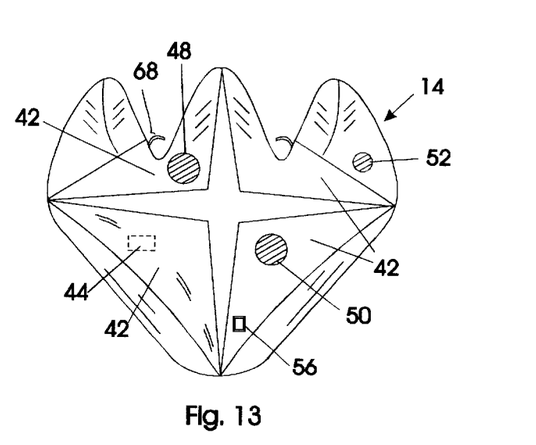
FIG. 13 is a top view of the auscultation piece used in the medical device of the present invention, in the disengageable and useable position.

The top surface or dorsal of the auscultation piece, as seen in FIGS. 1, 2, and 13 and as illustrated in the side view (FIGS. 9 and 12) includes at least one activation button or switch 48. This switch 48 is used to activate and/or deactivate the auscultation piece. When in use, this switch is depressed and when desired to deactivate the auscultation piece, this same button is pressed for terminating power transmission. Optionally, and in the preferred embodiment, this switch can be used for releasing or engaging the earpiece to the auscultation piece.

Optionally, a second switch 50 can be utilized in combination with the first switch. In this configuration, the first switch can be used to activate the unit, while the second switch can be used to deactivate the unit. Alternatively, both switches can be depressed simultaneously for allowing the unit to be activated or deactivated. In an alternative embodiment, a voice-activated unit can be used for activating the unit. Alternatively, and as is preferred, the switch can be coupled to a timer, which will initiate the transmission of sound after a pre-determined amount of time and if sound is not detected will automatically deactivate the unit. This arrangement will consequently provide a unit that is not only accurate in transmission of signals, but also one that conserves energy when not in use.

Once the system is activated, the user places the auscultation piece on the patient. When sound, such as the pulse of the patient, is received, an indicator 52 will activate. In the preferred embodiment, the indicator is a light source, such as a conventional LED, that flashes with each sound heard.

Figure 11:
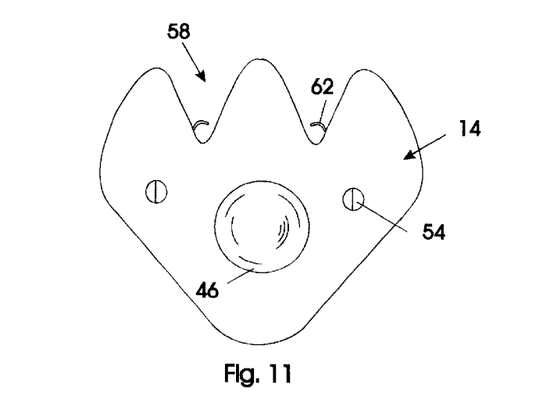
FIG. 11 is a bottom plan view of the auscultation piece used in the medical device of the present invention, in the disengageable and useable position.

To power the unit, conventional means are utilized. As seen in FIG. 11, batteries are stored and housed within the battery housing 54 and are utilized to power the auscultation piece.

Information, such as sound, is transmitted instantaneously to the earpiece via the main unit or chip 44. Optionally, the received data can be transmitted to a secondary source or any desired sources by coupling the unit to a computer or the like. To enable coupling, a data port 56 is utilized. Dependent upon the chip, which is used, the auscultation piece can include the capability of storing data. In this arrangement, the stored data can be downloaded via the hard wired port or data port 56. Downloading data is ideal for quickly receiving a second opinion, for medical record keeping, teaching and can enable a health care profession to transmit sound across for use in Tele medicine. The use of such a configuration will inherently increase the usability and capability of the medical apparatus of the present invention.

As seen in FIGS. 1, 2, 11 and 13, grooves 58 are located in the sidewall of the auscultation piece. These grooves are a receiving device and thus will receive the securing unit of the earpiece. As seen in FIGS. 1, 2, 3, and 6, the securing unit comprises at least one post or shaft 60. This post is received within at least one groove so as to rest therein and enable accurate placement of the auscultation piece and earpiece to the carrier. This post also acts as a stop, and thus when the auscultation piece is located within the holding case, the user can place the earpiece therein. When sliding the earpiece therein, the grooves will receive the post(s) and once received the post will prevent the earpiece from sliding further therein and thus prevent damage to the ear piece and/or auscultation piece.

As seen in FIG. 6, the top area of the posts can include an enlarged portion (illustrated, but not labeled). This enlarged portion will prevent the earpiece for dislodging for the auscultation piece.

Optionally, included can be a lockable device for locking the post to the auscultation piece. In one embodiment, the lockable device can be nuts and the posts can be threaded. Thus the user will rotate the nuts until it is secured within the unit. Optionally, conventional pivotal pins 62 can be used. As seen in FIG. 11, in this design, the user depresses a button 50 for allowing the pins to open and once the posts are located therein, the button is released, and the posts lock the pins within the grooves. Still a further lockable device would be to allow for the pins 62 to be spring loaded, so that the user merely pushes the posts on the pins to enable the post to fit into the recess portion. Once therein, the pins will pivot back to its original position. It is noted that the lockable device is designed to quickly lock the earpiece to the auscultation piece and thus will allow for any conventional unit that renders such a configuration.

Optionally, in the preferred embodiment, the earpiece can include shafts that will catch a hook. In this design, as seen in FIGS. 1, 2, and 13 extending outwardly from the grooves 58 of the auscultation piece 14 are spring loaded hooks 68 that are coupled to a release button 64. Optionally, these hooks can be coupled to one or both of the activation buttons, 48 and/or 50. In this configuration, if the user depresses the release button the hooks will raise inward or outward. This will provide for a clearance to exist between the shafts and the hook and permit the earpiece to be removed from or travel towards the auscultation piece. Releasing the button will provide for the hooks to return to its original position.

Figure 14:
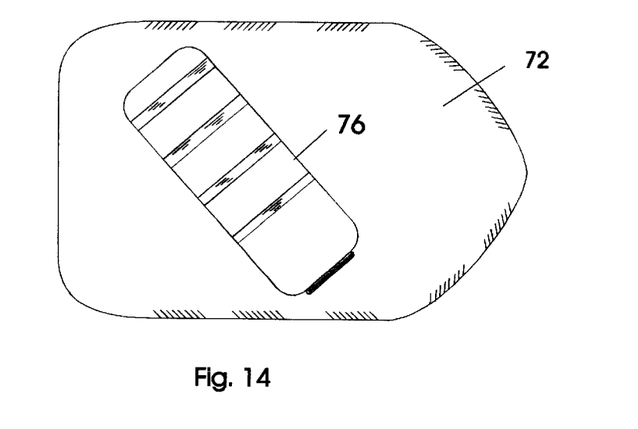
FIG. 14 is a bottom plan view of the holding case used for storing and maintaining the earpiece and auscultation piece when not in use.

The carrying case 16, as seen in FIGS. 1, 2 and 14 is designed to maintain the earpiece and auscultation piece when not in use and includes a top area 70 and a rear or back area 72. The top area includes upward and inward walls 74 that inherently form channels. These channels will slideably receive the outer ends of the auscultation piece and earpiece. The rear area includes a conventional attaching unit 76, such as a clip or the like, for attaching the device to the user, when not in use. This clip can be spring loaded, as illustrated.

Generally, when the carrying case is used, the unit (earpiece and auscultation piece) are secured therein providing the case to be in an upward and/or slightly forward position. This upward and slightly forward position will prevent the unit from disengaging from the carrying case.

To ensure placement of the unit therein, a lock, not illustrated, can be used. This lock can be a spring-loaded shaft. In operation, the shaft is depressed to provide for the unit to enter the carrying case or to prevent the unit from escaping and dislodging from the carrying case. This will protect the unit and prevent damage to occur therewith.

Figure 15:
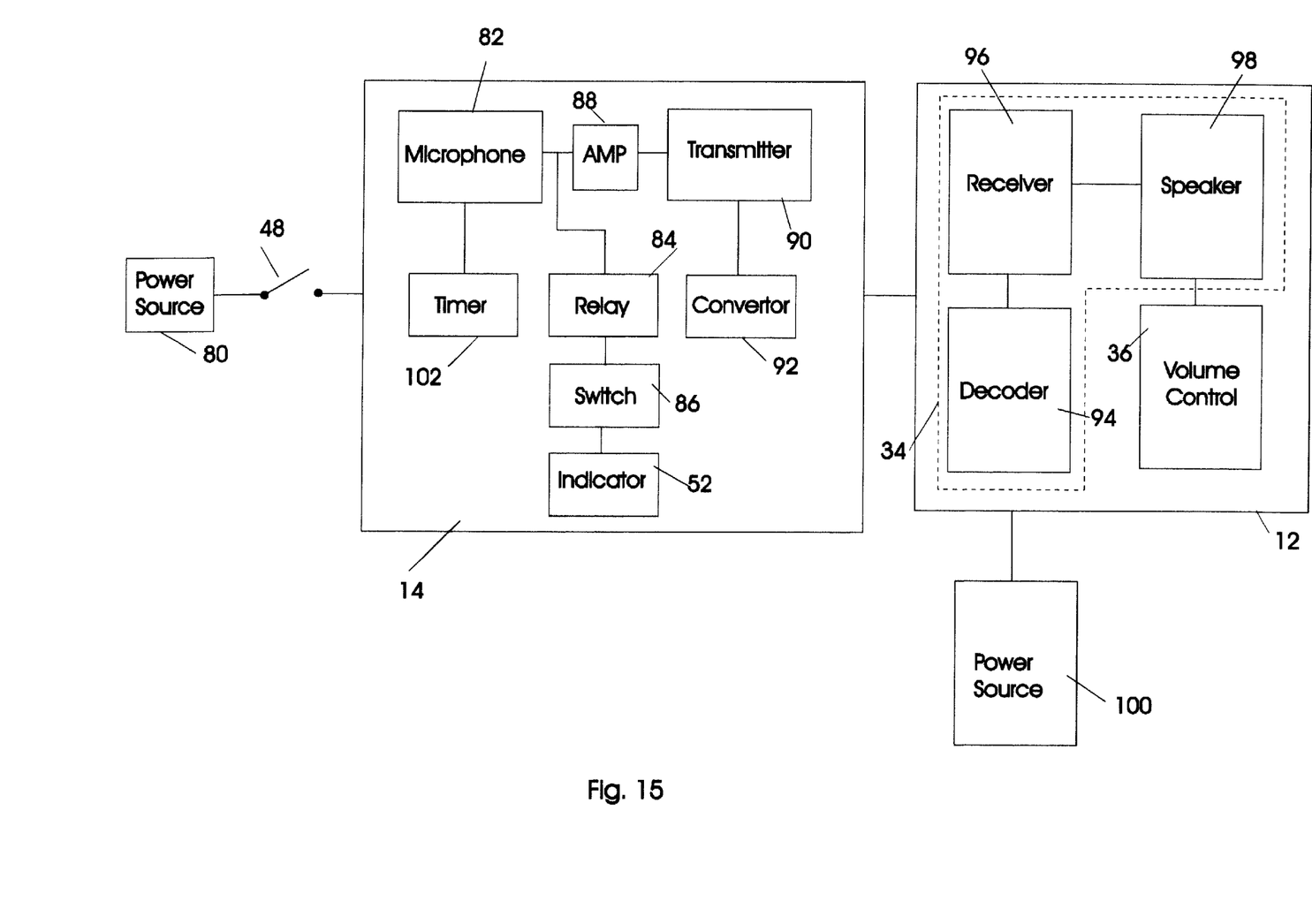
FIG. 15 is a block diagram illustrating the electrical components utilized with the medical device of the present invention.

The electrical components used for successful transmission of sound are illustrated in FIG. 15. As seen in this block diagram, the auscultation piece 14 is coupled to a power source 80 via a switch 48. It is noted that this switch can be coupled to two separate activation buttons. In this design, one switch will activate the unit (turn it on by providing a close circuit) and the second button will deactivate the unit (turn it off by providing an open circuit) or in a separate configuration, both buttons must be depressed simultaneously in order for activation to occur.

A microphone 82 is used to convert sound into electrical signals. Once sound is detected, the signals travel from the microphone to a relay 84. This relay will activate switch 86, which is coupled to an indicator 52. Thus, upon the detection of sound, the relay will cause the switch to close and allow current to travel to the indicator. The current will cause the indicator to activate and thus allow for a visual means when there is a presence of sound.

From the microphone 82 the signals are amplified via the amplifier 88, and used to modulate a carrier wave that has been generated by a transmitter 90. This modulated carrier is also amplified and then applied to a converter 92 for enabling the electrical signals to be converted to electromagnetic waves for transmission.

These electromagnetic waves are sent to the earpiece 12 and are intercepted and converted back to electrical signals via a decoder 94. These electrical signals are feed to a receiver 96 and separated from the carrier wave. Once separated, then are fed to a speaker 98, where they are converted into sound. The sound can be adjusted via conventional volume control means 36. The earpiece is powered via a power source 100.

It is noted that the decoder 94, receiver 96, and speaker 98 form the link manager receiver device 34. To enhance the final product, a timer 102 can be used to delay the time for power to be sent to the microphone.

To utilize the present invention, the practitioner, places the tips of his first three or four fingers on the grooves of the auscultation piece. Moving his arm upward, the practitioner removes the auscultation piece, which is still attached to the earpiece. Using the auscultation piece as a handle, the practitioner places the earpiece on his ear, with the soft hook catching the Pinna of the ear and setting the earpiece into position.

At this point, the release button is depressed, releasing the auscultation piece from the earpiece and activating the microphone for adequate operation. The lower portion of the auscultation piece is brought into place over the area to be listened. Appropriate transmission of sound occurs wireless, thus providing for sound to travel from the auscultation piece to the hearing portion of the earpiece.

After examination is completed, the activation button is pressed for termination of transmission. The release button is depressed to allow for the earpiece to mate with the auscultation piece. The mated pieces are slideably secured to the holding case for storage.

To enhance the final product, a microprocessor can be coupled with the link manager. Generally, dependent upon the chip (semi-conductor) that is used, the microprocessor may be included therein. If not, one can be coupled to the link manager. The use of a microprocessor will enable for the heard sound (data) to be stored therein. This data can then be transmitted to the desired location via the data port 56. Dependent on the microprocessor that is used, other data can be programmed into the present invention via the data port and stored within the microprocessor. It is noted that this microprocessor can be programmed to perform any desired task as deemed necessary by the user and innately provide for a medical apparatus with a plurality of options and usability.

While the invention has been particularly shown and described be understood by those skilled in the art that various changes in form and detail may be made without departing from with reference to an embodiment thereof, it will the spirit and scope of the invention.

I claim:

1. A wireless stethoscope comprising:

an auscultation piece;

at least one microphone housed within said auscultation piece;

a transmission system for wireless transmission of sound from the microphone;

a hearing device for wearing on a human ear, the hearing device having a receiver for receiving wireless transmission of sound from the microphone; and locking means for releaseably securing the hearing device to the auscultation piece, such that said auscultation piece may be grasped in one hand of a user and said hearing device released directly from the auscultation piece to a user's ear.

2. A wireless stethoscope according to claim 1, wherein: said hearing device further includes a frame having a J-shape configuration for receiving a user's ear, said frame having a distal end, and said hearing device further comprising a hearing portion at said distal end.

3. A wireless stethoscope according to claim 2, wherein: said hearing device has an adjusting device for adjusting the hearing portion with respect to the frame.

4. A wireless stethoscope according to claim 1, and further comprising:

a carrying case for removably receiving said auscultation piece and said hearing device.

5. A wireless stethoscope according to claim 4, wherein: said carrying case includes an attaching unit for attaching said carrying case to a user's clothing.

6. A wireless stethoscope according to claim 5, wherein: said carrying case further comprises at least two channels for receiving said auscultation piece and said hearing device.

7. A wireless stethoscope according to claim 6, wherein: said carrying case further comprises a stop for preventing said auscultation piece and said hearing device from dislodging when secured thereto.

8. A wireless stethoscope according to claim 1, wherein: said auscultation piece and said hearing device each include a power source.

9. A wireless stethoscope according to claim 8, wherein: said auscultation piece further comprises an activation switch for activating said auscultation power source.

10. A wireless stethoscope according to claim 9, wherein: said auscultation piece further comprises an indication device to indicate activation of said auscultation power source.

11. A wireless stethoscope according to claim 8, further comprising:

a timer, said timer coupled between said power source and said transmission system for activating transmission after a predetermined delaying time.

12. A wireless stethoscope according to claim 1, wherein: said auscultation piece has pyramidal shape including a plurality of recesses for receiving the tips of at least the first three fingers of a user's hand.

13. A wireless stethoscope according to claim 1, wherein: an attaching device is located on said hearing device for enabling said hearing device to be secured to a user.

14. A wireless stethoscope according to claim 1, wherein: said auscultation piece has a pyramidal shape forming a handle.

15. A wireless stethoscope according to claim 1, wherein: said auscultation piece further comprises a data port.

16. A wireless stethoscope according to claim 1, wherein: said hearing device further comprises a volume control device.

17. A wireless stethoscope comprising:

an auscultation piece;

at least one microphone housed within said auscultation piece;

a radio frequency chip housed within said auscultation piece and a transmission system for wireless transmission of sound from the microphone;

a hearing device, the hearing device having a receiver for receiving wireless transmission of sound from the microphone;

said auscultation piece and said hearing device each including a power source; and a timer coupled between said auscultation power source and said radio frequency chip for delaying activation time.

* * * * *